United States Patent
Senaras et al.

(10) Patent No.: US 11,612,311 B2
(45) Date of Patent: *Mar. 28, 2023

(54) SYSTEM AND METHOD OF OTOSCOPY IMAGE ANALYSIS TO DIAGNOSE EAR PATHOLOGY

(71) Applicant: Ohio State Innovation Foundation, Columbus, OH (US)

(72) Inventors: Caglar Senaras, Eindhoven (NL); Aaron Christopher Moberly, Columbus, OH (US); Theodoros Teknos, Powell, OH (US); Garth Fredric Essig, Jr., Columbus, OH (US); Charles Albert Elmaraghy, Dublin, OH (US); Nazhat Fatima Taj-Schaal, Lewis Center, OH (US); Lianbo Yu, Columbus, OH (US); Metin Nafi Gurcan, Winston-Salem, NC (US)

(73) Assignee: Ohio State Innovation Foundation, Columbus, OH (US)

( * ) Notice: Subject to any disclaimer, the term of this patent is extended or adjusted under 35 U.S.C. 154(b) by 60 days.

This patent is subject to a terminal disclaimer.

(21) Appl. No.: 17/188,681

(22) Filed: Mar. 1, 2021

(65) Prior Publication Data
US 2021/0228071 A1 Jul. 29, 2021

Related U.S. Application Data

(63) Continuation of application No. 16/329,903, filed as application No. PCT/US2017/049822 on Sep. 1, 2017, now Pat. No. 10,932,662.

(Continued)

(51) Int. Cl.
*A61B 1/227* (2006.01)
*A61B 1/00* (2006.01)
(Continued)

(52) U.S. Cl.
CPC ........ *A61B 1/227* (2013.01); *A61B 1/000094* (2022.02); *G06K 9/00* (2013.01);
(Continued)

(58) Field of Classification Search
CPC ....... A61B 1/00009; A61B 1/227; A61B 5/12; A61B 5/7264; G06K 9/00;
(Continued)

(56) References Cited

U.S. PATENT DOCUMENTS 10,182,711 B2 * 1/2019 Hoberman ............. A61B 5/004
2005/0276372 A1 12/2005 Bruder et al.
(Continued)

FOREIGN PATENT DOCUMENTS

JP 2005-349205 A 12/2005
JP 2012-176094 A 9/2012
(Continued)

OTHER PUBLICATIONS

European Patent Office. Communication pursuant to Article 94(3) EPC. Issued in European U.S. Appl. No. 17/847,614.9 dated Nov. 2, 2021. 4 pages.

(Continued)

*Primary Examiner* — Bobbak Safaipour
(74) *Attorney, Agent, or Firm* — Meunier Carlin & Curfman LLC

(57) ABSTRACT

Disclosed herein are systems and methods to detect a wide range of eardrum abnormalities by using high-resolution otoscope images and report the condition of the eardrum as "normal" or "abnormal."

22 Claims, 14 Drawing Sheets

Related U.S. Application Data

(60) Provisional application No. 62/382,914, filed on Sep. 2, 2016.

(51) Int. Cl.
 *G06K 9/00* (2022.01)
 *G06T 7/00* (2017.01)
 *A61B 5/12* (2006.01)
 *A61B 5/00* (2006.01)

(52) U.S. Cl.
 CPC .............. *G06T 7/0014* (2013.01); *A61B 5/12* (2013.01); *A61B 5/7264* (2013.01); *G06T 7/0012* (2013.01); *G06T 2207/10024* (2013.01); *G06T 2207/20081* (2013.01); *G06T 2207/20084* (2013.01); *G06T 2207/30004* (2013.01)

(58) Field of Classification Search
 CPC . G06T 2207/10024; G06T 2207/20081; G06T 2207/20084; G06T 2207/30004; G06T 7/0012; G06T 7/0014
 See application file for complete search history.

(56) References Cited

U.S. PATENT DOCUMENTS

| | | | |
|---|---|---|---|
| 2006/0077408 | A1 | 4/2006 | Amirghodsi |
| 2012/0218515 | A1 | 8/2012 | Imamura |
| 2014/0155748 | A1* | 6/2014 | Pern ..................... A61B 8/0875 600/443 |
| 2014/0249426 | A1* | 9/2014 | Huh ....................... A61B 1/227 600/473 |
| 2015/0065803 | A1* | 3/2015 | Douglas ............. A61B 1/00045 600/200 |
| 2015/0305609 | A1 | 10/2015 | Hoberman et al. |
| 2015/0351606 | A1 | 12/2015 | Ruppersberg |
| 2015/0363660 | A1 | 12/2015 | Vidal et al. |
| 2017/0209078 | A1* | 7/2017 | Hoberman .............. G16Z 99/00 |
| 2017/0296043 | A1 | 10/2017 | On |
| 2017/0323176 | A1* | 11/2017 | Lo ............................ G06F 16/58 |
| 2022/0261987 | A1* | 8/2022 | Gurcan ................ A61B 5/1032 |

FOREIGN PATENT DOCUMENTS

| | | |
|---|---|---|
| JP | 2016-510235 A | 4/2016 |
| WO | 2016/110993 A1 | 7/2016 |

OTHER PUBLICATIONS

Indian Patent Office. Office Action. Issued in Indian Application No. 201917008179 dated Nov. 25, 2021.6 pages.

Australian Intellectual Property Office Examination Report No. 1 issued in Australian Application No. 2017318691 dated Jul. 15, 2021. 4 pages.

Japanese Patent Office. Office Action issued in Japanese Application No. 2019-512207 dated Jun. 29, 2021. 12 pages including English translation.

Notice of Reasons for Refusal issued for Japanese Patent Application No. 2019-512207, dated Feb. 22, 2022.

Bishop, C.M., Pattern recognition. Machine Learning, 2006. 128.

Bookstein, F.L., Fitting conic sections to scattered data. Computer Graphics and Image Processing, 1979. 9(1): p. 56-71.

Breiman, L., Random forests. Machine learning, 2001. 45(1): p. 5-32.

Coimbra, M.T. and J.S. Cunha, MPEG-7 visual descriptors-contributions for automated feature extraction in capsule endoscopy. IEEE transactions on circuits and systems for video technology, 2006. 16(5): p. 628-637.

D. G. Lowe, "Distinctive image features from scale-invariant keypoints," International journal of computer vision, vol. 60, pp. 91-110, 2004.

E. Rublee, V. Rabaud, K. Konolige, and G. Bradski, "ORB: An efficient alternative to SIFT or SURF," in Computer Vision (ICCV), 2011 IEEE International Conference on, 2011, pp. 2564-2571.

Fawcett, T., An introduction to ROC analysis. Pattern recognition letters, 2006. 27(8): p. 861-874.

H. Bay, T. Tuytelaars, and L. Van Gool, "Surf: Speeded up robust features," Computer vision-ECCV 2006, pp. 404-417, 2006.

He, X. Zhang, S. Ren, and J. Sun, "Deep residual learning for image recognition," in Proceedings of the IEEE Conference on Computer Vision and Pattern Recognition, 2016, pp. 770-778.

Kuruvilla, A., et al., Automated Diagnosis of Otitis Media: Vocabulary and Grammar. International Journal of Biomedical Imaging, 2013. 2013: p. 1-15.

Lee, C.W., K. Jung, and H.J. Kim, Automatic text detection and removal in video sequences. Pattern Recognition Letters, 2003. 24(15): p. 2607-2623.

M. A. Fischler and R. C. Bolles, "Random sample consensus: a paradigm for model fitting with applications to image analysis and automated cartography," Communications of the ACM, vol. 24, pp. 381-395, 1981.

Mironică, I., C. Vertan, and D.C. Gheorghe. Automatic pediatric otitis detection by classification of global image features. 2011 E-Health and Bioengineering Conference (EHB), 19 pages.

Moberly, et al., "Digital otoscopy versus microscopy: How correct and confident are ear experts in their diagnoses? "Journal of Telemedicine and Telecare, p. 1357633X17708531, 2017.

Ozay, M. and F.T. Yarman-Vural, Hierarchical distance learning by stacking nearest neighbor classifiers. Information Fusion, 2016. 29: p. 14-31.

R. G. von Gioi, J. Jakubowicz, J.-M. Morel, and G. Randall, "LSD: A fast line segment detector with a false detection control," 1 EEE transactions on pattern analysis and machine intelligence, vol. 32, pp. 722-732, 2010.

Shie, C.-K., et al. A hybrid feature-based segmentation and classification system for the computer aided self-diagnosis of otitis media. 2014. IEEE.

Shie, C.-K., et al. Transfer representation learning for medical image analysis. 2015. IEEE.

Sikora, The MPEG-7 Visual Standard for Content Description—An Overview. IEEE Transactions on Circuits and Systems for Video Technology, vol. 11, No. 6, Jun. 2001, 696-702. doi: 10.1109/76.927422.

Szegedy, et al., "Inception-v4, inception-resnet and the impact of residual connections on learning," arXiv preprint arXiv: 1602.07261, 2016.

Szegedy, et al., "Rethinking the inception architecture for computer vision," in Proceedings of the IEEE Conference on Computer Vision and Pattern Recognition, 2016, pp. 2818-2826.

Tanaka, M., R. Kamio, and M. Okutomi. Seamless image cloning by a closed form solution of a modified poisson problem, in SIGGRAPH Asia 2012 Posters. 2012. ACM. doi>10.1145/2407156.2407173.

International Preliminary Report on Patentability issued for Application No. PCT/US2017/049822, dated Mar. 14, 2019, 8 pages.

International Search Report and Written Opinion, Application No. PCT/US2017/049822, dated Nov. 16, 2017, 11 pages.

Hadjis, Stefan, et al. "Omnivore: An optimizer for multi-device deep learning on cpus and gpus." arXiv preprint arXiv:1606.04487. Jun. 14, 2016. p. 1-36.

Senaras, Caglar, Mete Ozay, and Fatos T. Yarman Vural. "Building detection with decision fusion." IEEE journal of selected topics in applied earth observations and Yemote sensing 6.3 (2013): 1295-1304.

Extended European Search Report, issued by the European Patent Office in Application No. EP 17847614.9 dated Feb. 10, 2020. 8 pages.

Senaras, Caglar, et al. "Autoscope: automated otoscopy image analysis to diagnose ear pathology and use of clinically motivated eardrum features." Medical Imaging 2017: Computer-Aided Diagnosis. vol. 10134. International Society for Optics and Photonics, 2017.

(56) References Cited

OTHER PUBLICATIONS

Myburgh, Hermanus C., et al. "Otitis media diagnosis for developing countries using tympanic membrane image-analysis." EBioMedicine 5 (2016): 156-160.
Wang, Xin, Tulio A. Valdez, and Jinbo Bi. "Detecting tympanostomy tubes from otoscopic images via offline and online training." Computers in biology and medicine 61 (2015): 107-118.
CN Office Action relating to Chinese Application No. 201780067908.6, dated Nov. 3, 2022.
Japanese Patent Office. Notice of Reasons for Refusal. Issued in JP Application No. 2019-512207 dated Nov. 22, 2022. 6 pages including English translation.

* cited by examiner

SYSTEM AND METHOD OF OTOSCOPY IMAGE ANALYSIS TO DIAGNOSE EAR PATHOLOGY

CROSS REFERENCE TO RELATED APPLICATION

This application is a continuation of U.S. application Ser. No. 16/329,903 filed Mar. 1, 2019, which is a national stage application filed under 35 U.S.C. § 371 of PCT/US2017/049822 filed Sep. 1, 2017, which claims priority to and benefit of U.S. Provisional Patent Application Ser. No. 62/382,914 filed Sep. 2, 2016, all of which are fully incorporated by reference and made a part hereof.

GOVERNMENT SUPPORT CLAUSE

This invention was made with government support under award no. TR001070 awarded by the National Institutes of Health. The government has certain rights in the invention.

BACKGROUND

Ear infections, specifically acute infections of the middle ear (acute otitis media), are the most commonly treated childhood disease and account for approximately 20 million annual physician visits in the U.S. alone. The subjective nature of diagnosis results in a critical gap that needs to be addressed to improve diagnostic accuracy, by developing an objective method to assess the eardrum. A small number of previous studies in the literature have focused on computer-based eardrum analysis to assist in the objective diagnosis of ear pathology, but these studies were limited to the evaluation of otitis media while excluding other significant ear pathologies [1-4]. Development of more inclusive objective methods to identify eardrum abnormalities would assist clinicians in diagnosing or ruling out pathologies that may be subtle on clinical otoscopy (e.g., middle ear fluid).

Current works in ear pathology diagnosis as well as existing software tools are as follows: An early study attempt at developing computerized image analysis software by Mironică and colleagues focused exclusively on otitis media in pediatric cases [1]. The authors of that study investigated the performance of two color descriptors: HSV Color Histogram and HSV Color Coherence Vectors, by using different supervised classifiers. Their experiments showed that HSV Color Coherence Vector demonstrated better performance than the classical color histogram. However, the authors also concluded that color information alone was not sufficient for the identification of otitis cases. In a more recent study, Kuruvilla and colleagues developed a vocabulary and grammar system in order to classify a given eardrum image as acute otitis media (AOM), otitis media with effusion (OME) or no effusion (NOE) [2]. The algorithm started with a segmentation step, which aimed to localize the eardrum, followed by a step to reduce the effects of local illumination problems. Next, several representative features were extracted to represent clinical features such as bulging or translucency of the eardrum, or the presence of a bubble behind the eardrum. Finally, the images were classified using a hierarchical rule-based decision tree. Shie and colleagues proposed another approach to detect otitis media [3]. In order to separate the tympanic membrane from the input otoscope image, they introduced a modified two-stepped active contour segmentation method. Then the algorithm extracted several color and texture features like Gabor, Histogram of Gradient and Grid Color Moment. Each of these features was separately used for training different Support Vector Machine (SVM) classifiers. Finally, the prediction probabilities of the SVM classifiers were used as features by Adaboost for a final classification. In 2015, Shie and colleagues used a transfer learning paradigm for otitis media detection [4]. The authors extracted an unsupervised codebook from ImageNet images. Using the transfer-learned feature vectors, which were obtained by encoding otitis media images using the codebook, they employed supervised learning to learn a classifier from the labeled otitis media instances. Finally, they fused classification results with the results of some heuristic features (published in [3]) and improved their detection performance. Although the variation in the content and sizes of the databases and the focus of these previous studies make it difficult to objectively compare performance, the accuracies for these methods ranged from 73% [1] to 89% [2].

Recently, a study was conducted to examine diagnostic accuracy of experts using digital images collected using a handheld video otoscope system (see A. C. Moberly, M. Zhang, L. Yu, M. Gurcan, C. Senaras, T. N. Teknos, et al., "Digital otoscopy versus microscopy: How correct and confident are ear experts in their diagnoses?," Journal of Telemedicine and Telecare, p. 1357633X17708531, 2017, which is fully incorporated by reference). Diagnostic accuracy, inter-rater agreement, and levels of confidence were assessed for 12 otologists (ENT physicians with fellowship training in ear diseases) reviewing a subset of 210 ear images from the database. The otologists assigned diagnoses to images as normal or seven types of pathology. The overall accuracy rate for diagnosing ear pathologies was only 75.6%, as compared with the gold standard of otomicroscopy with objective assessments. Findings from this study provide further support for the need for objective computer-assisted image analysis (CAIA) approaches such as those described herein to assist clinicians in making more accurate ear diagnoses.

Objective methods to identify eardrum abnormalities would assist clinicians in making or ruling out diagnoses that are currently based on subjective information, particularly for pathologies that may be subtle on clinical otoscopy. Although some of the prior approaches [1-4] are promising, specifically for objective assessment of otitis media, currently none of them are able to identify more than one class of eardrum abnormality. Therefore, other clinically relevant abnormalities (e.g., tympanosclerosis or tympanic membrane retractions) would be detected as an "otitis media" or "normal" with these previous methodologies. A resulting misclassification could lead to improper clinical management of these pathologies.

Therefore, systems and methods are desired that overcome challenges in the art, some of which are described above. In particular, there is a need for a timely and accurate method and system to analyze otoscopy images in order to properly identify and classify any of a multitude of ear pathologies.

SUMMARY

Herein we disclose and describe novel automated otoscopy image analysis systems and methods. Presently, the system and method are designed to detect more than 14 eardrum abnormalities and report the condition of the eardrum as "normal" or "abnormal" and the type of abnormality (see FIGS. 1A-1E). Proof of concept has been performed using a centralized database of high resolution adult and pediatric images, captured via an otoscope from the Ear, Nose, and Throat (ENT) clinics at Ohio State University (OSU) and Nationwide Children's Hospital (NCH), as well as in a primary care setting (by Dr. Taj-Schaal). Unlike the previous studies, the disclosed approach aims to use a hybrid set of features: 1) clinically motivated eardrum features (CMEF) designed to characterize the symptoms in light of the clinical knowledge, and 2) several existing color, texture and shape features in the computer vision literature together. Computer vision features include Histogram of Gradient and Grid Color Moment features that were found to be useful in previous otitis media detection studies [3, 4], as well as the MPEG 7 descriptors, which have already demonstrated their robustness in content-based image retrieval. Although the MPEG 7 descriptors are analyzed in different biomedical image processing problems [5], this is the first study which evaluates the effectiveness of the MPEG7 descriptors for tympanic membrane images. Similarly, a new set of clinically motivated eardrum features are defined to recognize different types of abnormalities (like presence of a tympanostomy tube, cerumen, and/or perforation) and integrated into the framework. Finally, one of the state-of-the-art supervised ensemble learning classifiers, Fuzzy Stacked Generalization (FSG), creates a fusion space constructed by the decisions of multiple base-layer classifiers based on individual features [6]. Thus, rather than depending on the individual strength of each feature; diversity and collaboration of the features improve the overall classification performance.

Disclosed herein are methods for classifying tympanic membrane pathologies from images. One method comprises capturing one or more images of a tympanic membrane (e.g., eardrum) using an image capture device (e.g., a high-resolution digital otoscope); performing preprocessing on the captured one or more images; and classifying pathologies of the tympanic membrane using the captured one or more images.

Also disclosed herein are systems for classifying tympanic membrane pathologies from images. One such system comprises an image capture device (e.g., a high-resolution digital otoscope); a memory; and a processor in communication with the memory, wherein the processor executes computer-readable instructions stored in the memory that cause the processor to; perform preprocessing on the captured one or more images; and classify pathologies of the tympanic membrane using the captured one or more images.

Yet another aspect of the disclosures comprises a non-transitory computer-program product comprising computer executable code sections stored on a computer-readable medium, said computer executable code sections for performing a method of classifying tympanic membrane pathologies from images, comprising performing preprocessing on one or more images of a tympanic membrane (e.g., eardrum); and classifying pathologies of the tympanic membrane using the images.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 1A Tympanosclerosis, FIG. 1B Perforation, FIG. 1C Cerumen, FIG. 1D Retraction, and FIG. 1E Post-injection crust;

DETAILED DESCRIPTION

Figure 1A:
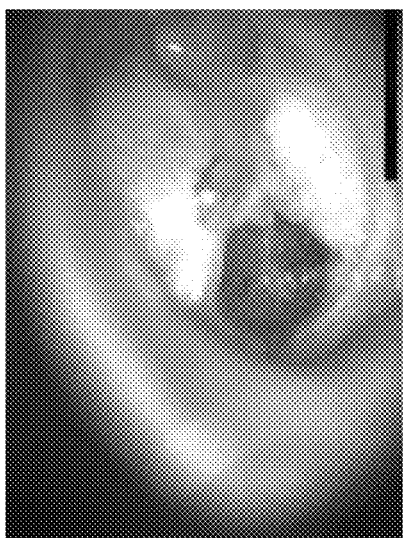
FIGS. 1A-1E are example photographic images for several abnormalities.
Figure 1B:
Figure 1C:
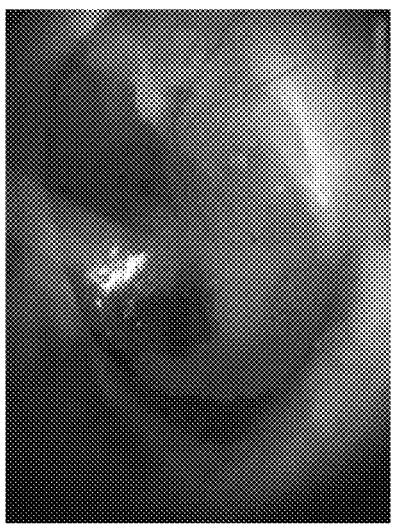
Figure 1D:
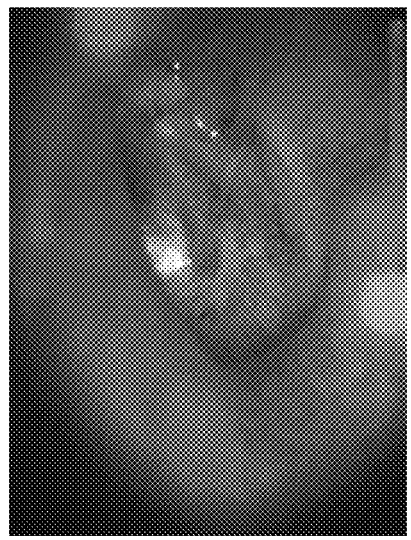
Figure 1E:
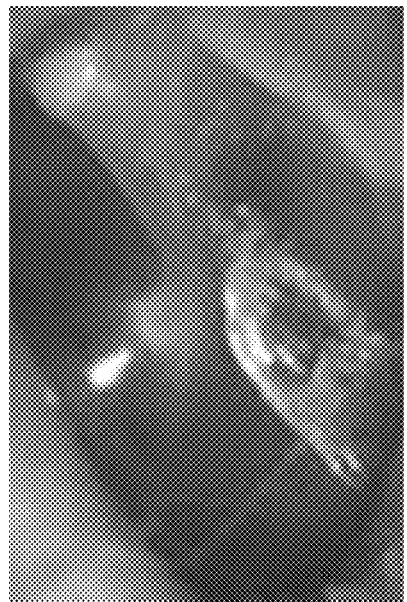

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

Figure 2:
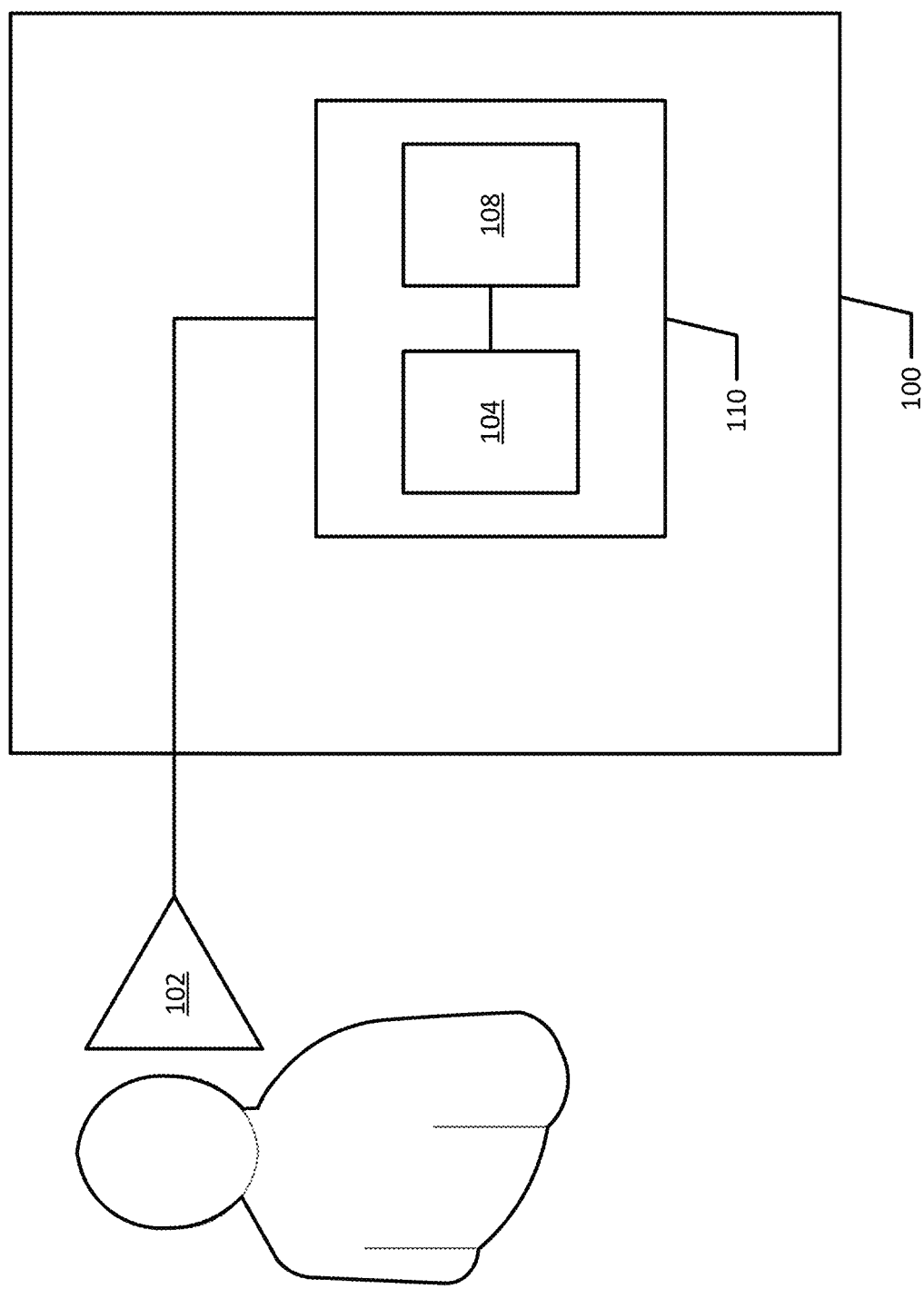
FIG. 2 illustrates an exemplary overview system for classifying eardrum pathologies from images.

FIG. 2 illustrates an exemplary overview system for classifying ear pathologies from images. As shown in FIG. 2, one embodiment of the system 100 comprises an image capture mechanism 102. In one aspect, the image capture mechanism 102 can be a camera. More specifically, the image capture mechanism 102 may be a digital otoscope. The image capture mechanism 102 can take still and/or video images. Generally, the image capture mechanism 102 will be a digital camera, but can be an analog device equipped with or in communication with an appropriate analog/digital converter. The image capture mechanism 102 may also be a webcam, scanner, recorder, or any other device capable of capturing a still image or a video.

As shown in FIG. 2, the image capture mechanism 102 is in direct communication with a computing device 110 through, for example, a network (wired (including fiber optic)), wireless or a combination of wired and wireless) or a direct-connect cable (e.g., using a universal serial bus (USB) connection, IEEE 1394 "Firewire" connections, and the like). In other aspects, the image capture mechanism 102 can be located remotely from the computing device 110, but capable of capturing an image and storing it on a memory device such that the image can be downloaded or transferred to the computing device 110 using, for example, a portable memory device and the like. In one aspect, the computing device 110 and the image capture mechanism 102 can comprise or be a part of a device such as a smart device, smart phone, tablet, laptop computer or any other fixed or mobile computing device.

In a basic configuration, the computing device 110 can be comprised of a processor 104 and a memory 108. The processor 104 can execute computer-readable instructions that are stored in the memory 108. Moreover, images captured by the image capture device 102, whether still images or video, can be stored in the memory 108 and processed by the processor 104 using computer-readable instructions stored in the memory 108.

The processor 104 is in communication with the image capture device 102 and the memory 108. The processor 104 can execute computer-readable instructions stored on the memory 108 to capture, using the image capture device 102, an image. In one aspect, the captured image can include an image of an eardrum of a subject.

The processor 104 can further execute computer-readable instructions stored on the memory 108 to capture, using the image capture device 102, one or more digital images and classify ear pathologies from the one or more images.

Figure 3A:
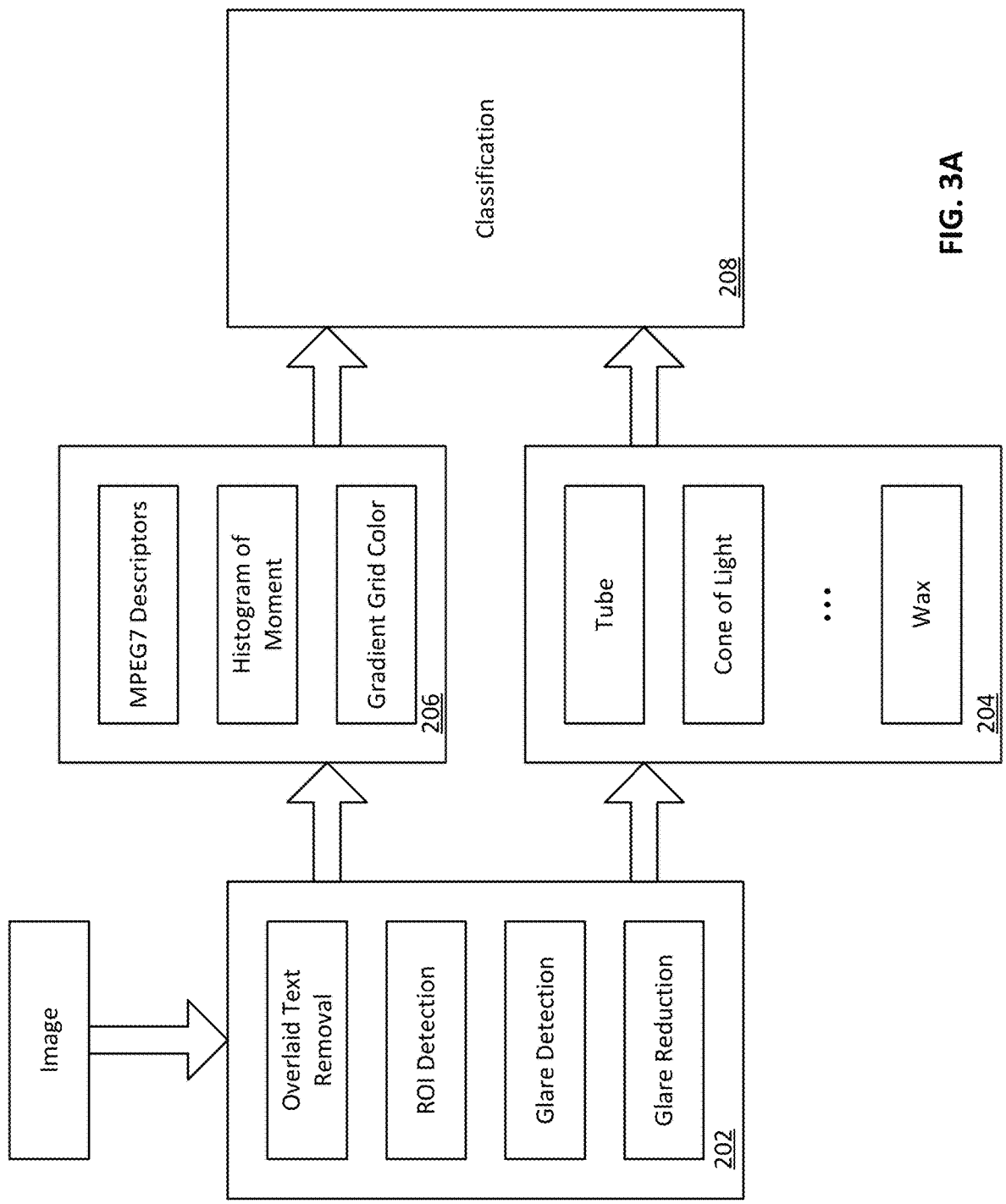
FIG. 3A illustrates modules that comprise an embodiment of an approach to classify ear pathologies.

FIG. 3A illustrates modules that comprise an embodiment of an approach to classify ear pathologies. These modules may comprise software, which can be executed by the processor 104. These modules comprise preprocessing 202;

extraction of clinically meaningful eardrum features (CMEF) 204; extraction of computer vision features (CVF) 206; and, classification with decision fusion 208. Each of these modules are described in greater detail herein.

An otoscope such as an HD video otoscope (e.g. JEDMED Horus+ HD Video Otoscope, St. Louis, Mo.) can be used to capture one or more images or videos of an eardrum. Although the higher resolution of collected HD images allows identification of some of the abnormalities, some of the design issues of this product may cause challenges for autonomous recognition. In the preprocessing module 202, these challenges are reduced and the images are prepared for computation of their features.

The acquisition of adequate images can be a challenging task because of visual obstruction (e.g., wax, hair), poor illumination, or a small field of view. If the patient is a child, there may also the problem of being able to capture a good still image while the patient is uncooperative. To solve these challenges, a new approach has been developed. In this approach, a short video (around 3-5 seconds) of the ear canal is captured. Then, software, executing the algorithm shown in FIG. 3B, analyzes video frames of the eardrum and creates a new mosaicked image (see FIG. 3C for a sample output).

Figure 3B:
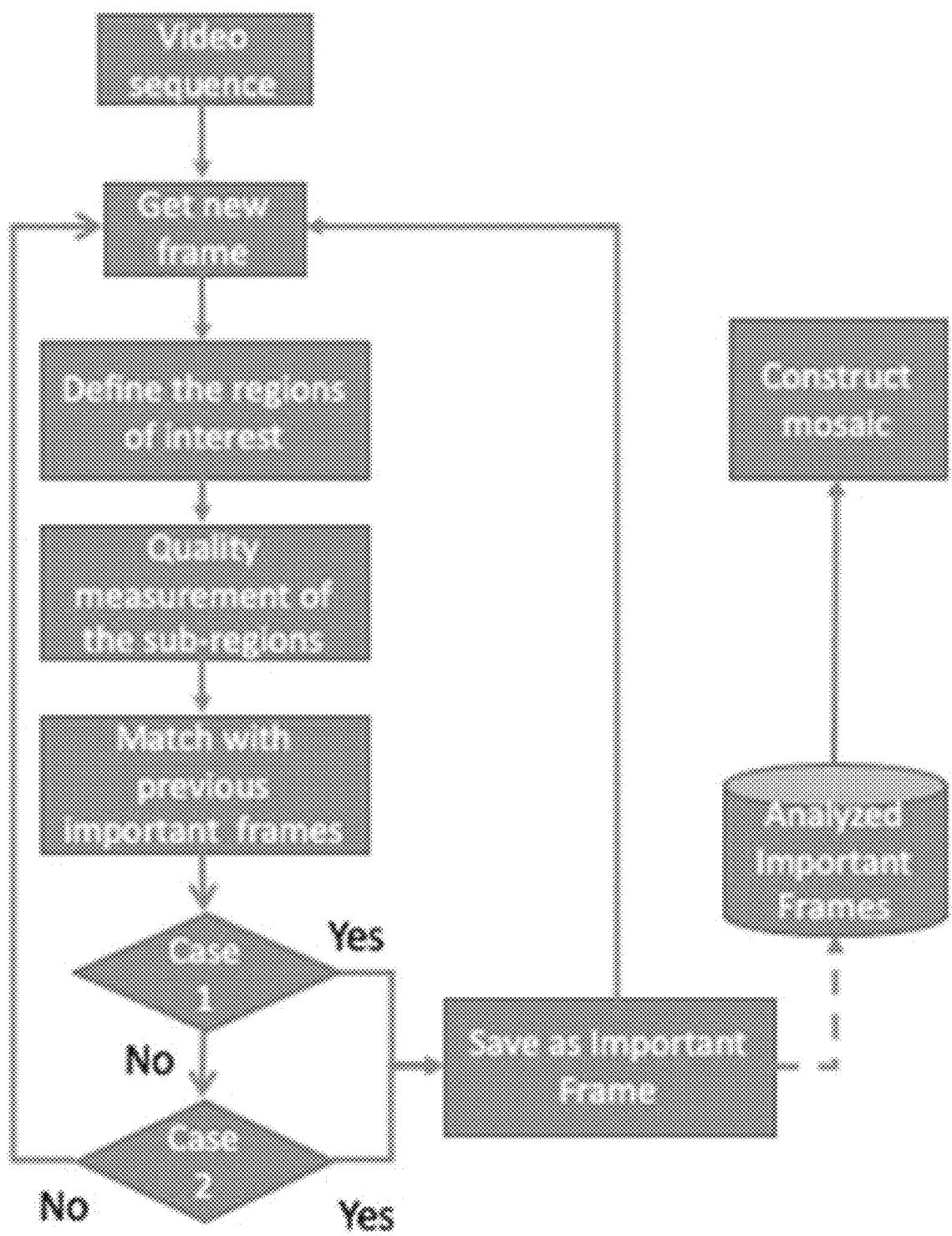
FIG. 3B illustrates a flow diagram for an exemplary composite image generation method where Case 1 occurs when a new frame includes new regions of interest which are not covered previously by another important frame, and Case 2 occurs if the region which is already covered by a previous important frame has a higher quality in this new frame.
Figure 3D:
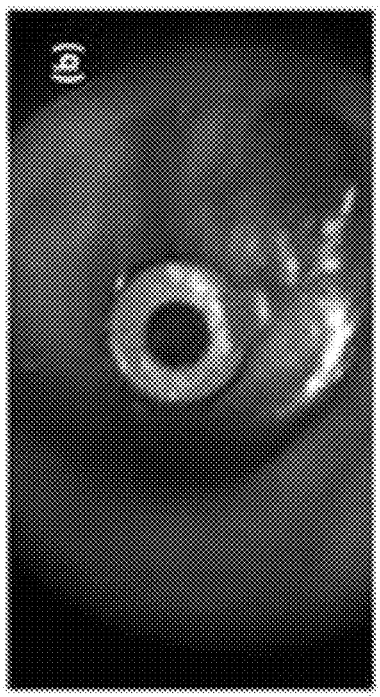
FIG. 3C-3F illustrate three sample frames from a five-second video clip (FIGS. 3C-3E) and the new composite image (FIG. 3F) where the composite image covers a much larger field-of-view and is affected less by blurring, obstruction by wax, or glare.

For each new frame in the video sequence, the mosaic image creation algorithm as described in FIG. 3B determines the regions of interest which are free of obstruction (e.g., wax, hair—detailed methods on how this is achieved is below). Each of these regions are divided into subsections, and the image quality in each section is evaluated in terms of being in-focus, having adequate contrast and illumination. If the frame includes the part of the eardrum that is not included in the previous frames, or includes an already included part of the eardrum but with higher quality (in terms of focus, contrast and illumination), then this frame is labeled as an "important frame" or otherwise identified. Finally, the new method constructs the mosaic image by considering the regions of interest in all the "important frames" in the video sequence.

The frames may include different amounts of visual obstruction (e.g., wax, hair, glare, etc.) and/or quality of illumination. As described herein, the method includes constructing composite obstruction-free images with excellent illumination. Therefore, the algorithm detects obstructions (wax, glare, and hair—see below) and out-of-focus regions during the composite image generation. To do that, the algorithm compares each new frame with the previous frames and updates the new image using the regions that are more in-focus and well-illuminated. To decide on in-focus and illumination quality, an image entropy is computed, and the frame with the highest entropy is selected.

Regarding wax detection, one of the typical characteristics of cerumen is its yellow color. Therefore, yellow regions are identified by using thresholding in CMYK color space. After these potential cerumen regions are detected as those regions with the highest "Y" values in the CMYK space, the mean and standard variation of the gradient magnitude of the intensities (i.e. "Y" values) of these cerumen regions are computed. These features are input to the FSG classifier to detect wax regions.

Glare is caused by the reflection of light from the otoscope on the surface of the tympanic membrane. Glare may be a problem for the calculation of some of the features (e.g., the mean color value of tympanic membrane). On the other hand, the cone of light, an important clinical diagnostic clue, can be inadvertently considered as glare by the glare detection algorithm and removed. In order to correctly extract the features, the disclosed method includes calculating the histogram of the intensity values and finds the peak corresponding to the highest intensity value in the histogram. That peak corresponds to the glare and cone of lights. To differentiate between the glare and cone of lights, area thresholding is applied (where glare(s) is larger than the cone of light(s)).

Hair detection includes detecting thin linear structures by using a line segment detector such as that described in R. G. von Gioi, J. Jakubowicz, J.-M. Morel, and G. Randall, "LSD: A fast line segment detector with a false detection control," IEEE transactions on pattern analysis and machine intelligence, vol. 32, pp. 722-732, 2010, which is incorporated by reference. Each hair strand is represented by two lines (both edges of the hair), approximately parallel to each other and the lines are close to each other. So, each approximately parallel line pair with a short distance is considered a hair candidate. The image texture is calculated between these parallel lines, and those with small textural variation are marked as hair.

In one of the embodiments, after the regions of interest are extracted, these regions are divided into 64×64 pixel blocks. For each block, the standard deviation, gray level co-occurrence matrix, contrast, and the mean intensity value are calculated. These values are weighted to calculate the tile quality. The weights may be determined manually or automatically.

To register two frames, points of interest are automatically extracted and the feature vectors for these points are matched. To extract points of interest, the performance of three state-of-the-art approaches is compared (see H. Bay, T. Tuytelaars, and L. Van Gool, "Surf: Speeded up robust features," Computer vision-ECCV 2006, pp. 404-417, 2006; D. G. Lowe, "Distinctive image features from scale-invariant keypoints," International journal of computer vision, vol. 60, pp. 91-110, 2004; and E. Rublee, V. Rabaud, K. Konolige, and G. Bradski, "ORB: An efficient alternative to SIFT or SURF," in Computer Vision (ICCV), 2011 IEEE International Conference on, 2011, pp. 2564-2571, each of which are fully incorporated by reference). In order to identify the matched points, the approach computes the distance between all possible pairs of detected features in two frames. The approach estimates the initial Homograph matrix with Random Sample Consensus (RANSAC) (see M. A. Fischler and R. C. Bolles, "Random sample consensus: a paradigm for model fitting with applications to image analysis and automated cartography," *Communications of the ACM*, vol. 24, pp. 381-395, 1981, which is also incorporated by reference).

Figure 3F:
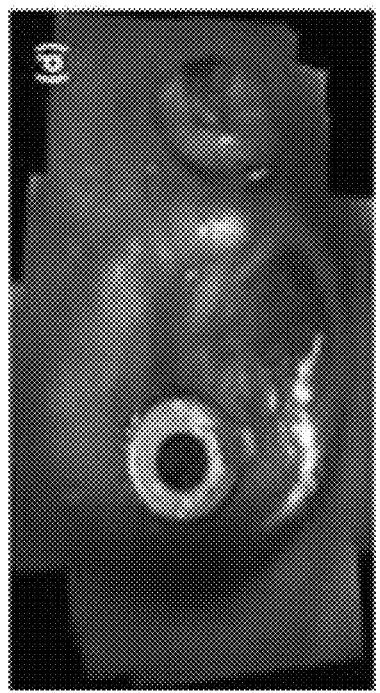
Figure 3C:
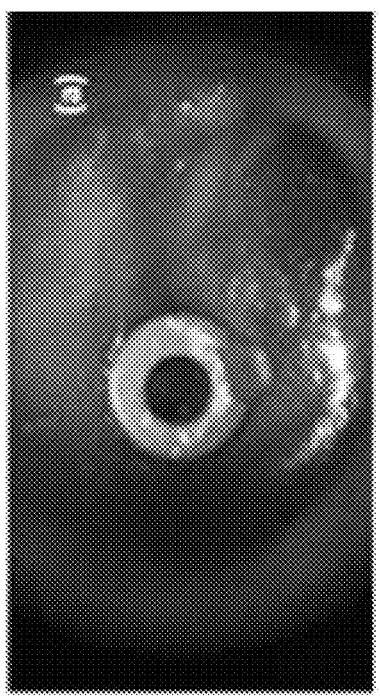
Figure 3E:
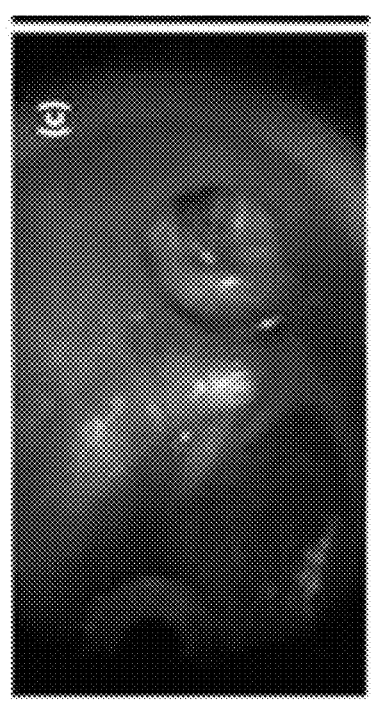

Each frame as an "important frame" or not according to two criteria: (1) If the new frame includes new regions of interest which are not covered previously by another important frame; or (2), if the region which is already covered by a previous important frame has a higher quality in this new frame. A composite image can then be created by stitching (FIG. 3F). The disclosed method uses 'important frames' during the composite image construction. The algorithm selects the most suitable "important frames" for subparts of the eardrum and use a multi-band blending (pyramid blending) method, which ensures smooth transitions between images despite illumination differences, while preserving high-frequency details.

Figure 4B:
FIGS. 4A-4C are photographs that illustrate removal of embedded text from an image of an eardrum.
Figure 4C:
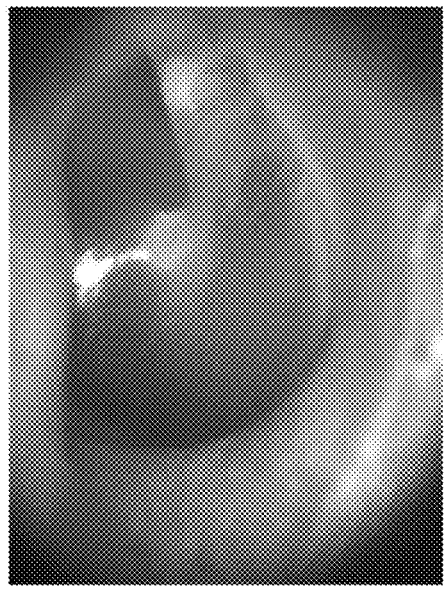
Figure 4A:

Returning to FIG. 3A, preprocessing may comprise embedded text removal. In many instances, images captured by an otoscope embeds the date and time information in the image for clinical purposes. In preprocessing, it may be desired to remove this embedded date and time information. Text detection and removal processes for still images and video sequences have been considered in the computer vision community [7]. However, unlike some of the existing studies, in order to detect the embedded text intensity ratios of the different bands and gradient information are used together. Due to the prior information about the possible location and color range of the text, this solution allows detection of text characters with a high recall rate. The detected text pixels are used to create a guidance field and the magnitude of the gradient is set to zero for these pixels. Finally, the overlaid text is seamlessly concealed [8] (FIGS. 4A-4C), resulting in the image of FIG. 4C.

Figure 5B:
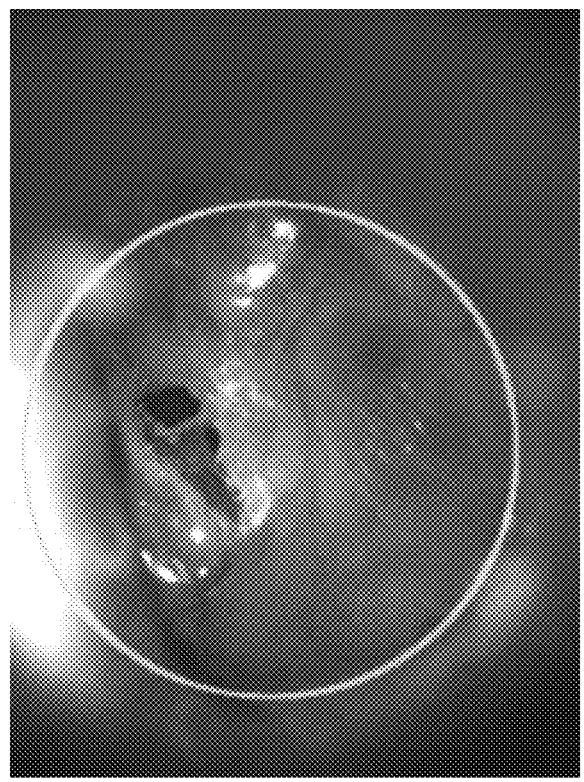
FIGS. 5A and 5B are photographs that illustrate identifying a region of interest (ROI) in an image of an eardrum.
Figure 5A:
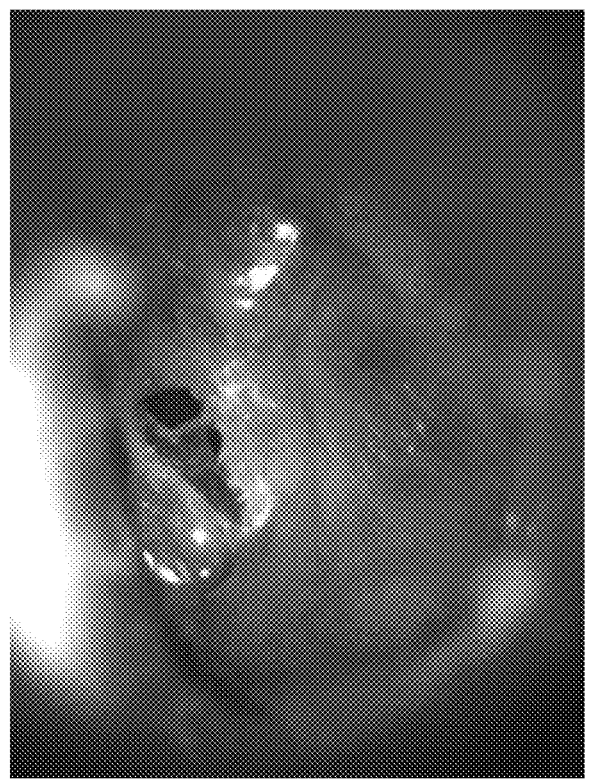

The preprocessing module 202 may further comprise region of interest (ROI) detection. The ROI, which includes the eardrum, can be in any location in the whole image due to the physical characteristics of the tip of the image capture device (e.g., otoscope) used. Also, the tip characteristic may cause some reflection problems at the boundary of the tip in the image (see FIGS. 5A and 5B). In order to solve this problem, the algorithm clusters all of the pixels according to their intensity values and then selects the background regions by considering the majority of pixels on the image boundary. After the background pixels are detected, the possible foreground pixels are fitted to an ellipse by using linear least square with Bookstein constraint [9]. Finally, a morphological erosion operation is applied to get rid of possible glare artifacts around the tip.

Figure 6B:
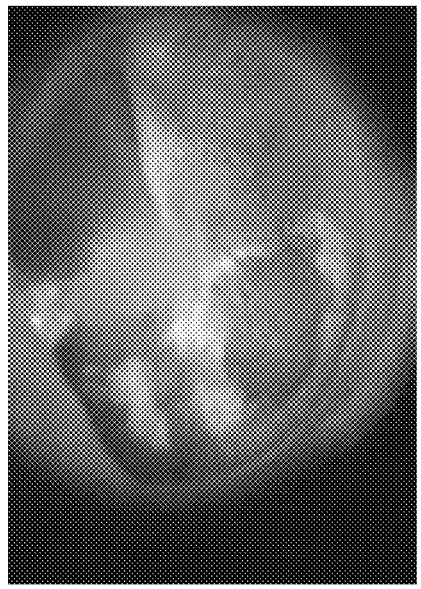
FIGS. 6A and 6B are photographs that illustrate detection of and removal of glare in an image of an eardrum.
Figure 6A:
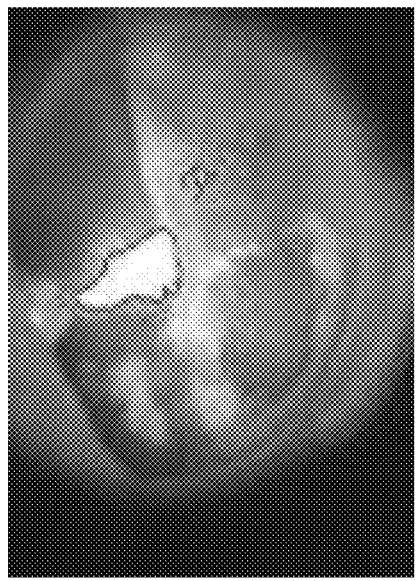

The preprocessing module 202 may also comprise glare detection and removal. One of the most critical artifacts in images is glare, caused by the reflection of light from the image capture device (e.g., otoscope, including a high-resolution digital otoscope) on the surface of the tympanic membrane. Glare may be a challenge for the calculation of some of the features (e.g., the mean color value of tympanic membrane). On the other hand, the cone of light, an important clinical diagnostic clue, can be inadvertently considered as glare by the glare detection algorithm and removed. In order to correctly extract the features, a histogram of the intensity values is calculated and finds the related peak in the histogram that corresponds to the glare. After the glare detection, the algorithm creates a modified copy of the image where detected regions of glare are seamlessly blended to the rest of the image by using the method in [8] (see, for example, FIGS. 6A and 6B).

The modules illustrated in FIG. 3 further comprise extraction of Clinically Motivated Eardrum Features (CMEF) 204. CMEF comprises of a set of handcrafted features such as the existence and the location of cone of light, visibility of malleus, protrusion of membrane, existence of tympanostomy tube, existence of wax, and the like, which are defined to characterize the symptoms in light of clinical knowledge used to define abnormalities and normality.

The extraction of computer vision features (CVF) module 206 may comprise the use of MPEG 7 visual descriptors, which have already demonstrated their robustness in content-based image retrieval, histogram of moment, and grid color gradient features as computer vision features. See T. Sikora, "The MPEG-7 visual standard for content description—an overview," in IEEE Transactions on Circuits and Systems for Video Technology, vol. 11, no. 6, pp. 696-702, June 2001. doi: 10.1109/76.927422, which is fully incorporated by reference.

The classification model 208 may comprise the use of a two-layer decision fusion technique, called Fuzzy Stacked Generalization (FSG) [6], for detecting abnormalities, since it allows us to use the advantages of complementary features instead of strong features. In the base-layer, each feature space is separately utilized by an individual classifier to calculate class membership vector. Then the decisions of the base-layer classifiers, class membership values, are aggregated to construct a new space, which is fed to a meta-layer classifier. The comparison with different classifiers is provided in the examples section of this specification.

FSG can also be used for multi-class classification to identify multiple types of ear pathology: e.g. AOM, middle ear effusion (non-infected fluid), cholesteatoma (a common destructive skin cyst in the ear), eardrum perforation, and eardrum retraction vs normal. Accordingly, the same two-layer decision fusion FSG technique is modified for abnormality type identification, since it allows the use of the advantages of complementary features instead of strong features. The fuzzy class membership values are used in order to estimate confidence level.

Alternatively or additionally, deep learning can be used to classify eardrum abnormalities. The neural network may use the output of the first method, original video clip and metadata (e.g. age and sex of the patient). The method may include at least one of the following networks: (1) an existing network model, i.e. ResNet-50[8], Inception v3 [9], or Inception-Resnet [10] which is already trained on a different dataset (like imagenet), is used for transfer learning (see K. He, X. Zhang, S. Ren, and J. Sun, "Deep residual learning for image recognition," in *Proceedings of the IEEE Conference on Computer Vision and Pattern Recognition*, 2016, pp. 770-778; C. Szegedy, V. Vanhoucke, S. Ioffe, J. Shlens, and Z. Wojna, "Rethinking the inception architecture for computer vision," in *Proceedings of the IEEE Conference on Computer Vision and Pattern Recognition*, 2016, pp. 2818-2826; and C. Szegedy, S. Ioffe, V. Vanhoucke, and A. Alemi, "Inception-v4, inception-resnet and the impact of residual connections on learning," *arXiv preprint arXiv: 1602.07261*, 2016, each of which are fully incorporated by reference). (2) A new deep learning network designed and trained with unsupervised and supervised approaches. (3) An ensembling neural network to combine two or more different classification approaches.

Alternatively or optionally, machine learning can be used to retrieve images of similar eardrum cases for classification of eardrum pathologies. This embodiment of the method can be used by clinicians with different levels of experience and expertise. Although the decision support provided by the deep-learning tool described above would be sufficient for many clinicians, some (particularly those with less experience) may need additional help in making their final diagnosis. For those clinicians, providing them with a selection of similar-looking images with already established ground truth would be helpful. In this method, such a tool is described which uses content-based image retrieval (CBIR) methodology.

Figure 7:
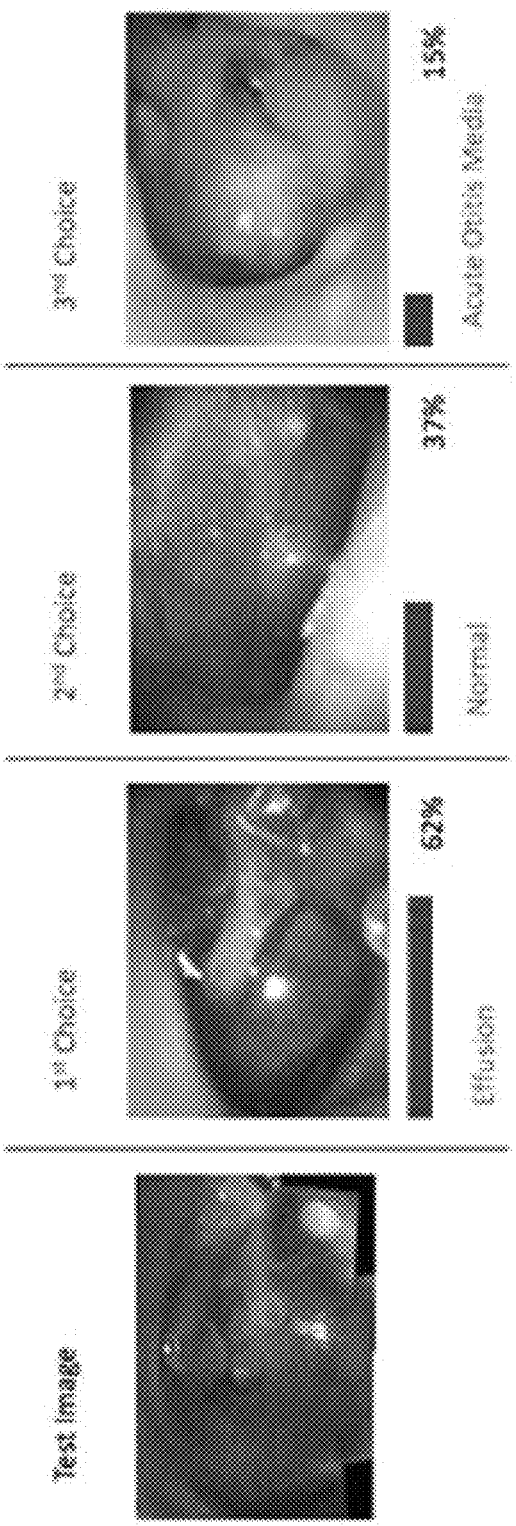
FIG. 7 is an example of content-based image retrieval for an ear with a diagnosis of middle ear effusion.

The question of image similarity has important applications in the medical domain because diagnostic decision-making has traditionally involved using evidence from a patient's data (image and metadata) coupled with the physician's prior experiences of similar cases. Content-based image retrieval is an image search technique that uses quantifiable (objectively calculated) features as the search criteria. The disclosed approach is based on deep learning techniques. FIG. 7 is an example of content-based image retrieval for an ear with a diagnosis of middle ear effusion. As can be seen in FIG. 7, the likelihood of effusion (62%) based on the comparison of the test image with images of ear pathologies using CBIR is much greater than the likelihood of a normal ear (37%) or acute otitis media (15%).

CBIR algorithms search for similar images by analyzing their visual content. As disclosed herein, rather than relying on hand-crafted features, a deep learning based solution learns features directly from images. The disclosed deep learning method employs convolutional neural networks (CNN). The last three fully connected layers of CNN can be used to extract features. Additionally, the CNN results are compared with those of different types of deep learning structures.

Conventional CBIR approaches typically choose rigid distance functions on low-level features for multimedia similarity searches, such as using Euclidean distance. However, the fixed rigid similarity/distance function may not always be optimal when the features are complex. Instead of directly measuring distance in extracted feature space, similarity learning (SL) algorithms are used. In order to learn the similarity metric, a pairwise ranking model is employed. For training sample i, $d_i=(p_i, p_i^+p_i^-)$ is called a triplet, where $p_i$, $p_i^+p_i^-$ are the query image, positive image, and negative image, respectively. The hinge loss for a triplet is defined and aims to minimize overall loss, the triple-based ranking loss function. Finally, metadata information is a common complement to image features in general, as well as medical content-based image retrieval research. The age and ethnicity of the patient, symptoms/temperature, previous otologic history, and other non-image data can be incorporated to add semantic information to image features as a means of reducing the semantic gap.

Figure 8:
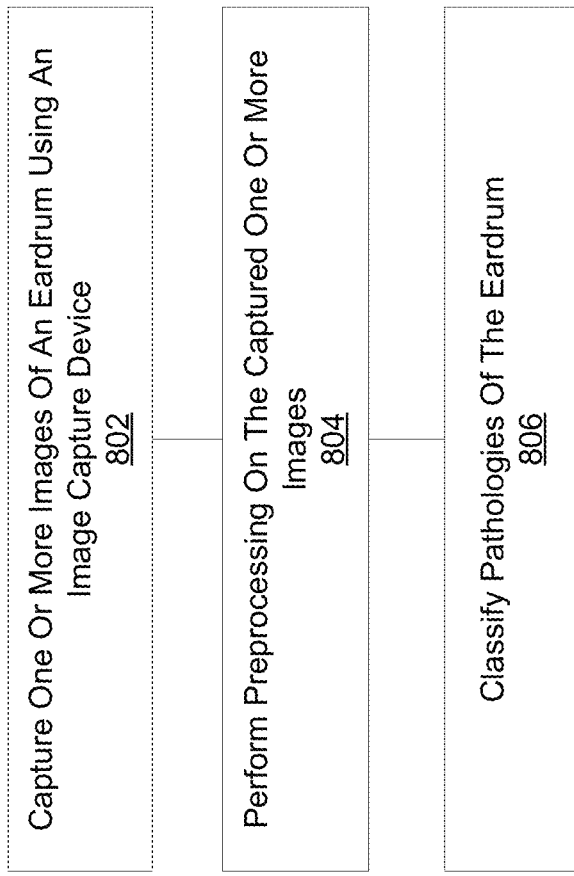
FIG. 8 is a flowchart that illustrates an exemplary method of classifying eardrum pathologies.

FIG. 8 is a flowchart that illustrates an exemplary method of classifying ear pathologies. In one embodiment, the method comprises 802 capturing one or more images or videos of an eardrum using an image capture device (e.g., an otoscope). In one aspect, the one or more images comprise one or more high-resolution otoscope images. At 804, pre-processing is performed on the captured one or more images. Preprocessing steps may include preprocessing steps for reducing sensor based problems, selecting a region of interest in the one or more images, detecting light reflections and creating a copy of the one or more images where these glare effects are reduced. Preprocessing may also include generating a composite image, as described above, to remove blurring, wax, glare, hair, etc. At 806, classifying pathologies of the eardrum is performed. One of the embodiments of classifying pathologies may comprise extracting computer vision features (CVF) from the one or more images. One or more of visual MPEG-7 descriptors, Histogram of Gradient, and Grid Color Moment features are used to extract color, texture and shape information. Clinically meaningful eardrum features (CMEF) are extracted from the one or more images. The clinically motivated eardrum features identify some of the clues for abnormalities and normality from the one or more images. Classifying the pathologies of the eardrum may be performed with decision fusion using the CMEF and CVF. The CVF and CMEF information was fused by a two-layered stacked generalization algorithm (FSG) that focuses on complementary features instead of strong features. Other embodiments of methods of classification of the pathologies may also include automated identification of abnormalities using deep learning and/or CBIR that utilizes deep learning features and training a pairwise ranking model, both as described above. Step 806 is performed using a processor of a computing device, as described below.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for discriminating tissue of a specimen. In one exemplary aspect, the units can comprise a computing device that comprises a processor 921 as illustrated in FIG. 9 and described below.

Figure 9:
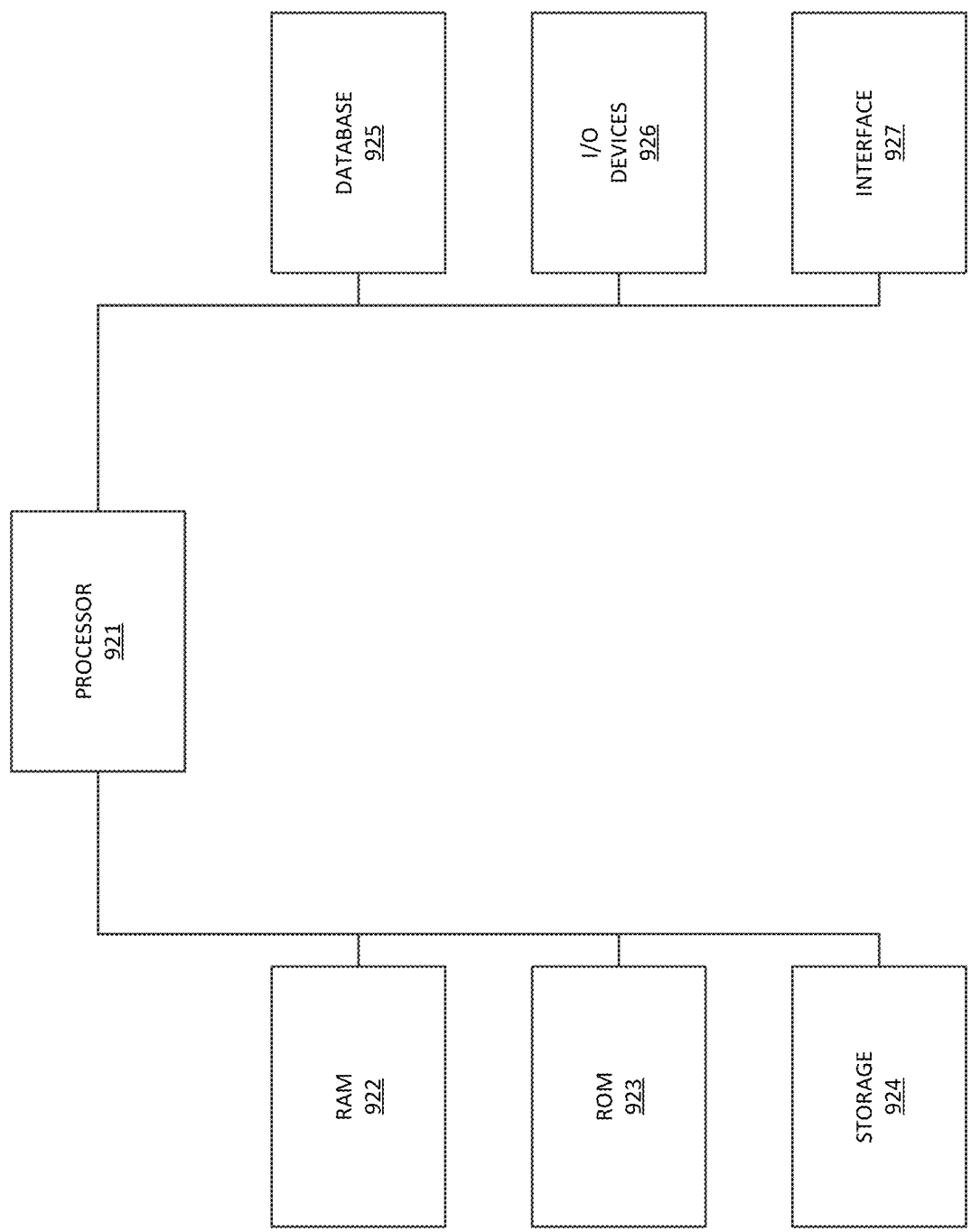
FIG. 9 illustrates an exemplary computer that can be used for classifying tympanic membrane pathologies from images.

FIG. 9 illustrates an exemplary computer that can be used for classifying tympanic membrane pathologies from images. As used herein, "computer" may include a plurality of computers. The computers may include one or more hardware components such as, for example, a processor 921, a random access memory (RAM) module 922, a read-only memory (ROM) module 923, a storage 924, a database 925, one or more input/output (I/O) devices 926, and an interface 927. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 824 may include a software partition associated with one or more other hardware components. It is understood that the components listed above are exemplary only and not intended to be limiting.

Processor 921 may include one or more processors, each configured to execute instructions and process data to perform one or more functions associated with a computer for classifying pathologies of an eardrum based upon one or more images of the eardrum. Processor 921 may be communicatively coupled to RAM 922, ROM 923, storage 924, database 925, I/O devices 926, and interface 927. Processor 921 may be configured to execute sequences of computer program instructions to perform various processes. The computer program instructions may be loaded into RAM 922 for execution by processor 921.

RAM 922 and ROM 923 may each include one or more devices for storing information associated with operation of processor 921. For example, ROM 923 may include a memory device configured to access and store information associated with the computer, including information for identifying, initializing, and monitoring the operation of one or more components and subsystems. RAM 922 may include a memory device for storing data associated with one or more operations of processor 921. For example, ROM 923 may load instructions into RAM 922 for execution by processor 921.

Storage 924 may include any type of mass storage device configured to store information that processor 921 may need to perform processes consistent with the disclosed embodiments. For example, storage 924 may include one or more magnetic and/or optical disk devices, such as hard drives, CD-ROMs, DVD-ROMs, or any other type of mass media device.

Database 925 may include one or more software and/or hardware components that cooperate to store, organize, sort, filter, and/or arrange data used by the computer and/or processor 921. For example, database 925 may store digital images of an eardrum along with computer-executable instructions for preprocessing the one or more images; extracting clinically meaningful eardrum features (CMEF) from the one or more images; extracting computer vision features (CVF) from the one or more images; and, classifying pathologies of the eardrum with decision fusion using the CMEF and CVF and/or computer-executable instructions for automated identification of abnormalities using deep learning and/or CBIR that utilizes deep learning features and training a pairwise ranking model. It is contemplated that database 925 may store additional and/or different information than that listed above.

I/O devices 926 may include one or more components configured to communicate information with a user associated with computer. For example, I/O devices may include a console with an integrated keyboard and mouse to allow a user to maintain a database of digital images, results of the analysis of the digital images, metrics, and the like. I/O devices 926 may also include a display including a graphical user interface (GUI) for outputting information on a monitor. I/O devices 926 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 927 may include one or more components configured to transmit and receive data via a communication network, such as the Internet, a local area network, a workstation peer-to-peer network, a direct link network, a wireless network, or any other suitable communication platform. For example, interface 927 may include one or more modulators, demodulators, multiplexers, demultiplexers, network communication devices, wireless devices, antennas, modems, and any other type of device configured to enable data communication via a communication network.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

In an exemplary study, 247 tympanic membrane images of adult and pediatric patients were collected including 113 images having abnormalities. The images were captured via an HD otoscope (JEDMED Horus+ HD Video Otoscope, St. Louis, Mo.) from the Ear, Nose, and Throat (ENT) clinics at Ohio State University (OSU) and Nationwide Children's Hospital (NCH), as well as in a primary care setting (by Dr. Taj-Schaal). The images were of size 1440 by 1080 pixels, and were compressed using JPEG. The data collection phase of this study is on-going.

Performance Evaluation

Classification performance is evaluated based on the "ground-truth" generated by expert otolaryngologists. In the experiment, an n-fold cross validation technique was used with n=20. Results were evaluated in terms of sensitivity, specificity, and accuracy metrics [10].

Results and Discussion

Figure 10B:
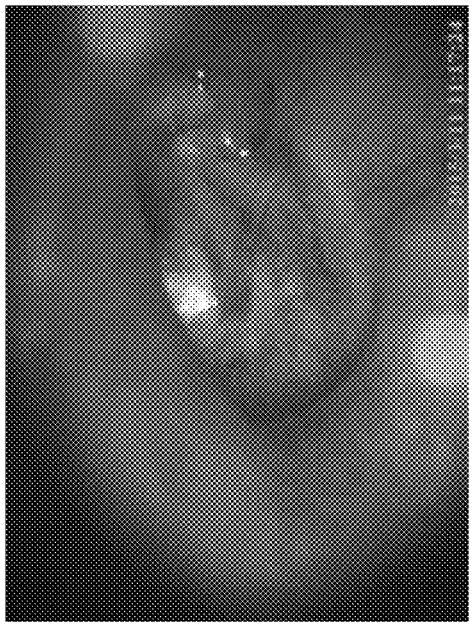
FIGS. 10A-10C are photographs that illustrate images of correctly classified abnormal eardrums.
Figure 10C:
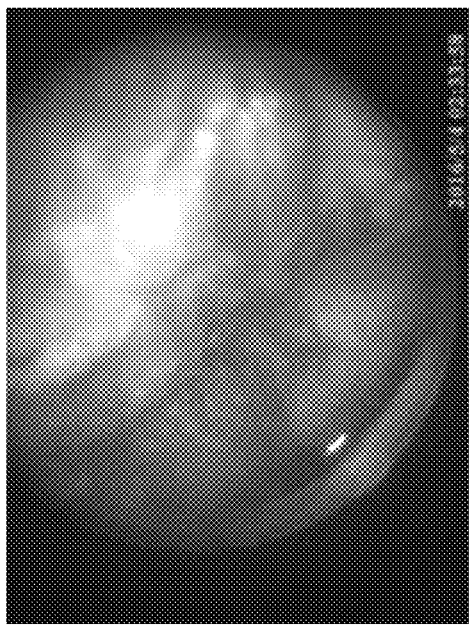
Figure 10A:
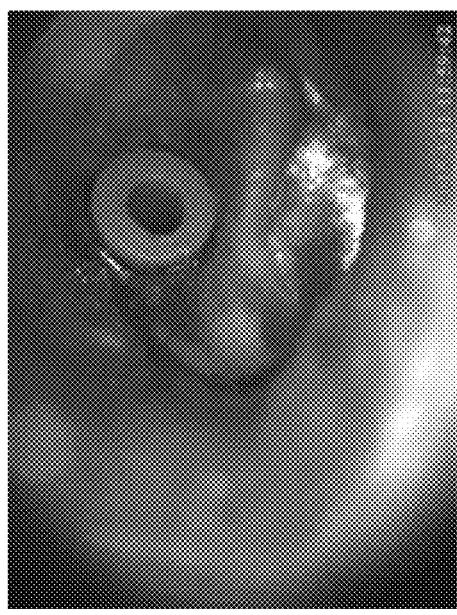
Figure 11B:
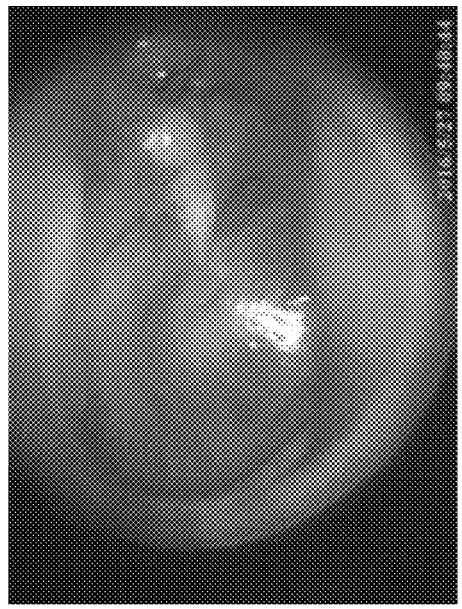
FIGS. 11A-11C are photographs that illustrate include three of the 17 normal eardrums that were incorrectly classified as abnormal.
Figure 11C:
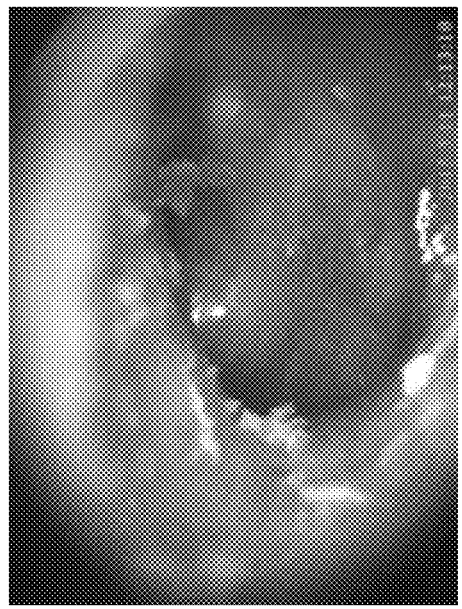
Figure 11A:
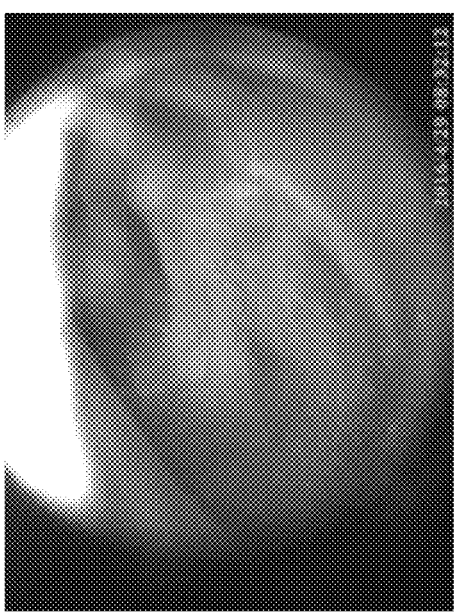
Figure 12A:
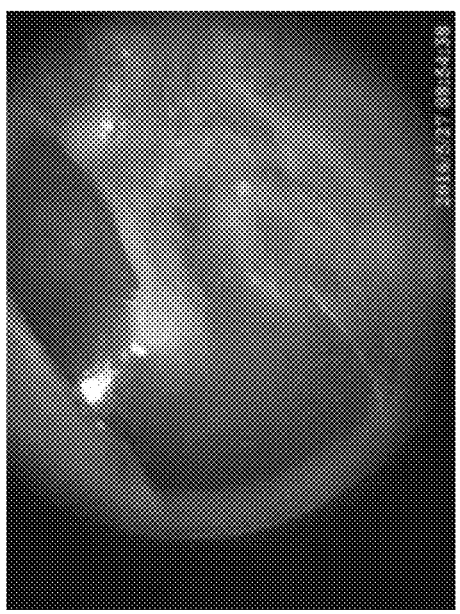
FIGS. 12A-12C are photographs that illustrate abnormal eardrums that were incorrectly classified as normal.
Figure 12B:
Figure 12C:
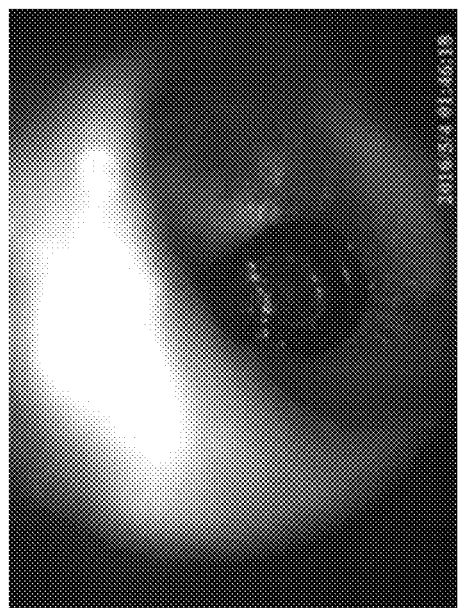

The confusion matrix of the preliminary results of the described system and method is given in Table 1. FIGS. 10A-10C illustrate images of correctly classified abnormal eardrums. FIGS. 11A-11C include three of the 17 normal eardrums, classified as abnormal. Similarly, three misclassified abnormal eardrum are shown in FIGS. 12A-12C.

TABLE 1

Confusion Matrix for FSG Confusion Matrix Confusion Matrix

|  |  | Computer Classification | |
|---|---|---|---|
|  |  | Normal | Abnormal |
| Ground Truth | Normal | 117 | 17 |
|  | Abnormal | 21 | 92 |

Additionally, the robustness of the selected decision fusion technique was explored. For this purpose, the classification performance of the FSG compared to Support Vector Machine (SVM) [11] and Random Forest classifiers (RF)[12] (Table 2) was evaluated.

TABLE 2

Comparison of Different Classifiers

|  | Sensitivity | Specificity | Accuracy |
|---|---|---|---|
| FSG | 87.3% | 81.4% | 84.6% |
| RF | 79.9% | 77.0% | 78.5% |
| Linear SVM | 59.7% | 68.1% | 63.6% |

The preliminary results based on this dataset show that the proposed approach is very promising for "normal" versus "abnormal" classification. In these preliminary experiments, the disclosed system and method was able to classify the given 247 tympanic membrane images as a normal or abnormal with approximately 84.6% accuracy. According to these experiments, visual MPEG-7 features are very promising for classification of tympanic membrane images. However, CMEF may also be required in order to improve the performance for some of the abnormalities.

References (all of which are incorporated by reference, unless otherwise noted):
1. Mironică, I., C. Vertan, and D. C. Gheorghe. Automatic pediatric otitis detection by classification of global image features. 2011. IEEE.
2. Kuruvilla, A., et al., Automated Diagnosis of Otitis Media: Vocabulary and Grammar. International Journal of Biomedical Imaging, 2013. 2013: p. 1-15.
3. Shie, C.-K., et al. A hybrid feature-based segmentation and classification system for the computer aided self-diagnosis of otitis media. 2014. IEEE.
4. Shie, C.-K., et al. Transfer representation learning for medical image analysis. 2015. IEEE.
5. Coimbra, M. T. and J. S. Cunha, MPEG-7 visual descriptors-contributions for automated feature extraction in capsule endoscopy. IEEE transactions on circuits and systems for video technology, 2006. 16(5): p. 628.
6. Ozay, M. and F. T. Yarman-Vural, Hierarchical distance learning by stacking nearest neighbor classifiers. Information Fusion, 2016. 29: p. 14-31.
7. Lee, C. W., K. Jung, and H. J. Kim, Automatic text detection and removal in video sequences. Pattern Recognition Letters, 2003. 24(15): p. 2607-2623.

8. Tanaka, M., R. Kamio, and M. Okutomi. Seamless image cloning by a closed form solution of a modified poisson problem. in SIGGRAPH Asia 2012 Posters. 2012. ACM.
9. Bookstein, F. L., Fitting conic sections to scattered data. Computer Graphics and Image Processing, 1979. 9(1): p. 56-71.
10. Fawcett, T., An introduction to ROC analysis. Pattern recognition letters, 2006. 27(8): p. 861-874.
11. Bishop, C. M., Pattern recognition. Machine Learning, 2006. 128.
12. Breiman, L., Random forests. Machine learning, 2001. 45(1): p. 5-32.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby fully incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of classifying tympanic membrane pathologies, comprising:
performing preprocessing on a plurality of images of a tympanic membrane to produce one or more composite images, wherein regions of interest are selected from each of the plurality of images or a subset of the plurality of images and the selected regions of interest are used to form the one or more composite images;
extracting computer vision features (CVF) and clinically motivated eardrum features (CMEF) from the one or more composite images; and
classifying pathologies of the tympanic membrane using the CVF and CMEF information, wherein classifying pathologies of the tympanic membrane using the CVF and CMEF information comprises classifying pathologies of the tympanic membrane using the CVF and CMEF information fused by a two-layered stacked generalization algorithm that focuses on complementary features instead of strong features.

2. The method of claim 1, wherein the plurality of images are captured using an image capture device.

3. The method of claim 2, wherein the image capture device comprises a video image capture device and each of the plurality of images are frames captured from a video of the tympanic membrane.

4. The method of claim 1, wherein preprocessing comprises detecting obstructions in and/or illumination of each of the images that comprise the plurality of images.

5. The method of claim 4, wherein the detected obstructions and/or illumination are used in selecting the regions of interest.

6. The method of claim 5, wherein the regions of interest selected from each of the plurality of images or the subset of the plurality of images are free from the obstructions such that the one or more produced composite images do not include the obstructions.

7. The method of claim 4, wherein the obstructions comprise one or more of blurring, wax, glare, and hair in the video frames.

8. The method of claim 1, wherein the two-layered stacked generalization algorithm comprises using a Fuzzy Stacked Generalization (FSG) classifier.

9. The method of claim 1, wherein the preprocessing on the plurality of images of a tympanic membrane to produce one or more composite images includes one or more of reducing sensor based problems, selecting the regions of interest in the video frames, detecting glare effects, and creating a copy of the video frames with reduced glare effects.

10. The method of claim 1, wherein extracting the CVF from the one or more composite images comprises using one or more of visual MPEG-7 descriptors, Histogram of Gradient, and Grid Color Moment features to extract color, texture and shape information from the one or more composite images.

11. The method of claim 1, wherein the CMEF identify clues for abnormalities and normality of the tympanic membrane from the one or more composite images.

12. The method of claim 1, wherein CMEF comprises a location of a cone of light, a visibility of malleus, a protrusion of membrane, an existence of tympanostomy tube, or an existence of wax.

13. The method of claim 1, wherein classifying pathologies of the tympanic membrane using the using the CVF and CMEF information comprises using deep learning for the automated identification of abnormalities.

14. The method of claim 13, wherein the deep learning comprises deep learning networks including Inception V3 or ResNet.

15. The method of claim 13, wherein the abnormalities include one or more of acute otitis media (AOM), middle ear effusion (non-infected fluid), cholesteatoma (a common destructive skin cyst in the ear), eardrum perforation, and eardrum retraction vs normal.

16. The method of claim 1, wherein classifying pathologies of the tympanic membrane using the using the CVF and CMEF information comprises using content-based image retrieval (CBIR) to compare the using the CVF and CMEF information to a library of images to identify abnormalities.

17. The method of claim 16, wherein the abnormalities include one or more of acute otitis media (AOM), middle ear effusion (non-infected fluid), cholesteatoma (a common destructive skin cyst in the ear), eardrum perforation, and eardrum retraction vs normal.

18. A method of classifying tympanic membrane pathologies, comprising:
performing preprocessing on a plurality of images of a tympanic membrane to produce one or more composite images, wherein regions of interest are selected from each of the plurality of images or a subset of the plurality of images and the selected regions of interest are used to form the one or more composite images;

extracting computer vision features (CVF) and clinically motivated eardrum features (CMEF) from the one or more composite images; and classifying pathologies of the tympanic membrane using the CVF and CMEF information, wherein an image entropy is calculated and the images with highest entropy values are selected from the plurality of images to produce the one or more composite images.

19. A system for classifying tympanic membrane pathologies, comprising:
a memory; and
a processor in communication with the memory, wherein the memory contains computer-executable instructions that when executed by the processor cause the processor to:
perform preprocessing on a plurality of images of a tympanic membrane to produce one or more composite images, wherein regions of interest are selected from each of the plurality of images or a subset of the plurality of images and the selected regions of interest are used to form the one or more composite images;
extract computer vision features (CVF) and clinically motivated eardrum features (CMEF) from the one or more composite images; and
classify pathologies of the tympanic membrane using the CVF and CMEF information, wherein classifying pathologies of the tympanic membrane using the CVF and CMEF information comprises classifying pathologies of the tympanic membrane using the CVF and CMEF information fused by a two-layered stacked generalization algorithm that focuses on complementary features instead of strong features.

20. A computer program product with computer-executable instructions embodied on a non-transitory computer readable medium, wherein the computer-executable instructions when executed by a computer perform a process of classifying tympanic membrane pathologies comprising:
performing preprocessing on a plurality of images of a tympanic membrane to produce one or more composite images, wherein regions of interest are selected from each of the plurality of images or a subset of the plurality of images and the selected regions of interest are used to form the one or more composite images;
extracting computer vision features (CVF) and clinically motivated eardrum features (CMEF) from the one or more composite images; and
classifying pathologies of the tympanic membrane using the CVF and CMEF information, wherein classifying pathologies of the tympanic membrane using the CVF and CMEF information comprises classifying pathologies of the tympanic membrane using the CVF and CMEF information fused by a two-layered stacked generalization algorithm that focuses on complementary features instead of strong features.

21. A system for classifying tympanic membrane pathologies, comprising:
a memory; and
a processor in communication with the memory, wherein the memory contains computer-executable instructions that hen executed by the processor cause the processor to:
perform preprocessing on a plurality of images of a tympanic membrane to produce one or more composite images, wherein regions of interest are selected from each of the plurality of images or a subset of the plurality of images and the selected regions of interest are used to form the one or more composite images;
extract computer vision features (CVF) and clinically motivated eardrum features (CMEF) from the one or more composite images; and
classify pathologies of the tympanic membrane using the CVF and CMEF information, wherein an image entropy is calculated and the images with highest entropy values are selected from the plurality of images to produce the one or more composite images.

22. A computer program product with computer-executable instructions embodied on a non-transitory computer readable medium, wherein the computer-executable instructions when executed by a computer perform a process of classifying tympanic membrane pathologies comprising:
performing preprocessing on a plurality of images of a tympanic membrane to produce one or more composite images, wherein regions of interest are selected from each of the plurality of images or a subset of the plurality of images and the selected regions of interest are used to form the one or more composite images;
extracting computer vision features (CVF) and clinically motivated eardrum features (CMEF) from the one or more composite images; and
classifying pathologies of the tympanic membrane using the CVF and CMEF information, wherein an image entropy is calculated and the images with highest entropy values are selected from the plurality of images to produce the one or more composite images.

* * * * *